United States Patent
Holt et al.

(10) Patent No.: US 9,446,094 B2
(45) Date of Patent: Sep. 20, 2016

(54) METHOD FOR PROCESSING PROLAMIN-CONTAINING FEED FOR A RUMINANT ANIMAL TO POTENTIATE MILK PRODUCTION OR CONCEPTION

(71) Applicants: Mark D. Holt, Pheonix, AZ (US); Matthew R. Garner, Houston, TX (US)

(72) Inventors: Mark D. Holt, Pheonix, AZ (US); Matthew R. Garner, Houston, TX (US)

( * ) Notice: Subject to any disclaimer, the term of this patent is extended or adjusted under 35 U.S.C. 154(b) by 62 days.

(21) Appl. No.: 13/732,210

(22) Filed: Dec. 31, 2012

(65) Prior Publication Data

US 2013/0172241 A1 Jul. 4, 2013

Related U.S. Application Data

(60) Provisional application No. 61/582,347, filed on Dec. 31, 2011.

(51) Int. Cl.
| | |
|---|---|
| *A23K 1/18* | (2006.01) |
| *A23L 1/20* | (2006.01) |
| *A23L 1/05* | (2006.01) |
| *A23L 1/00* | (2006.01) |
| *A23P 1/00* | (2006.01) |
| *A61K 38/16* | (2006.01) |

(52) U.S. Cl.
CPC .......... *A61K 38/168* (2013.01); *A23K 20/147* (2016.05); *A23K 20/163* (2016.05); *A23K 40/20* (2016.05); *A23K 50/10* (2016.05)

(58) Field of Classification Search
USPC ........................................................ 426/2, 46
IPC ................. A61K 38/168; A23K 1/003,1/1631, A23K 1/1643, 1/1813, 1/1653, 1/18, 1/004
See application file for complete search history.

(56) References Cited

PUBLICATIONS

Blezinger., "Grain Processing Has Positive Affects on Production—Parrt II" Available online at www.cattletoday.com on Oct. 1, 2005.*

* cited by examiner

*Primary Examiner* — Erik Kashnikow
*Assistant Examiner* — Assaf Zilbering
(74) *Attorney, Agent, or Firm* — Polsinelli PC (57) ABSTRACT

Composition and method for processing prolamin-containing feed source into a low-vitreous gelatinous feedstuff. The feedstuff is fed to ruminant animals for the purpose of potentiating either milk production and/or conception. The feed source can be corn and the ruminant animal can be a bovine, and might be a cow. The method includes processing, by extrusion, a prolamin-containing feed source having a starch-protein matrix within which the included protein is composed of at least 3% percent prolamin. This processing produces a hydrophilic gelatinous feedstuff that has starch and protein content. The hydrophilic low-vitreous gelatinous feedstuff is fed to a ruminant animal. A rumen-retained portion of the fed feedstuff is retained within the rumen of the animal for at least a twenty-four hour period, and during the first twenty-four hours of that period, at least seventy-five percent of the starch content of the rumen-retained portion of the fed feedstuff is digested.

36 Claims, 6 Drawing Sheets

METHOD FOR PROCESSING PROLAMIN-CONTAINING FEED FOR A RUMINANT ANIMAL TO POTENTIATE MILK PRODUCTION OR CONCEPTION

CROSS REFERENCE TO RELATED APPLICATIONS

This application claims the benefit under 35 U.S.C. §119 (e) of U.S. Provisional Patent Application No. 61/582,347, filed on Dec. 31, 2011, which is incorporated herein by reference in its entirety; a copy is simultaneously filed herewith, and which also constitutes a portion of the present disclosure as part of this patent's specification.

BACKGROUND

Figure 1:
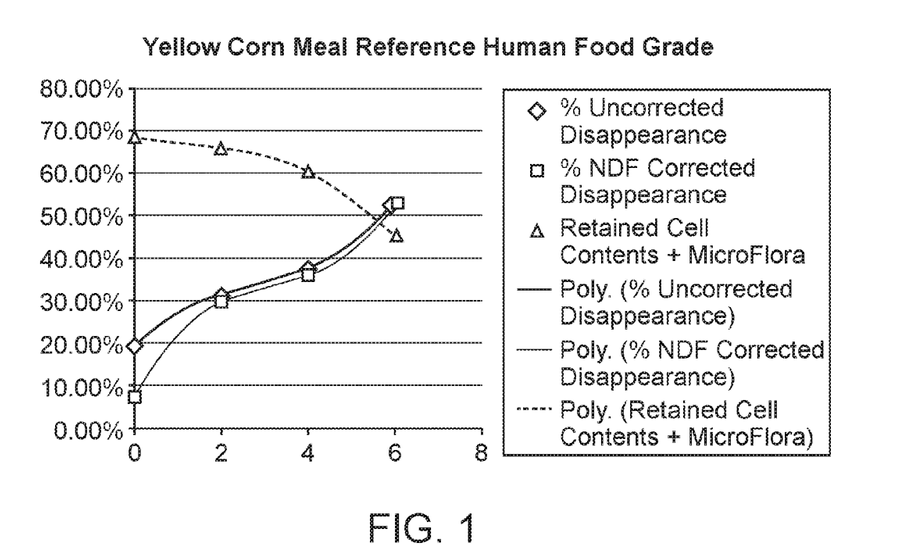
FIG. 1 graphically depicts certain percentage based measurements taken at 0, 2, 4, and 6 hours of yellow corn meal Reference Human Food Grade NDF digests of rumen digestion residue samples
Figure 2:
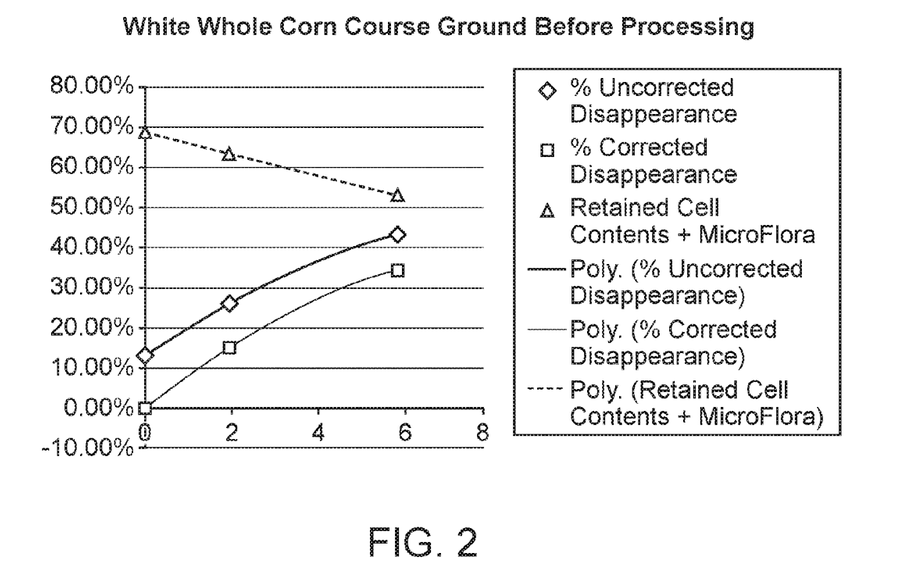
FIG. 2 depicts similar measurements, but for white whole corn, course ground before processing.
Figure 3:
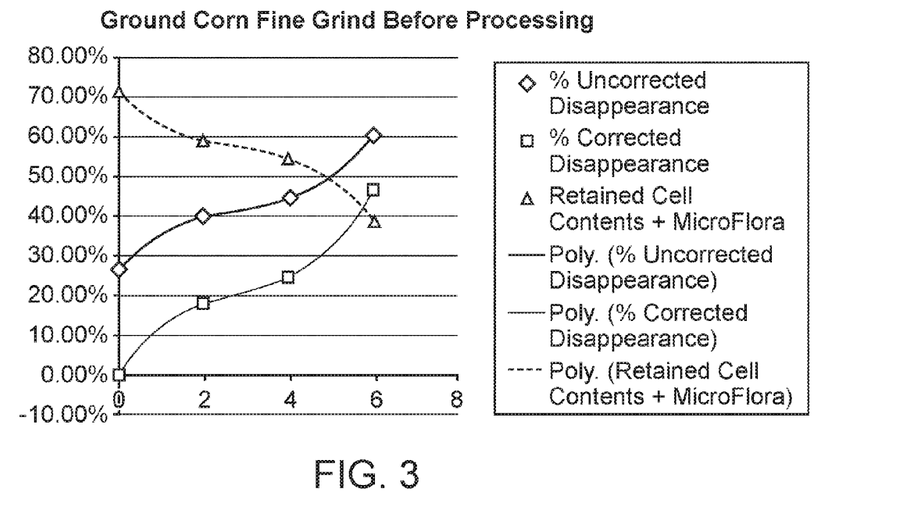
FIG. 3 depicts similar measurements, but for ground corn, fine grind before processing.
Figure 4:
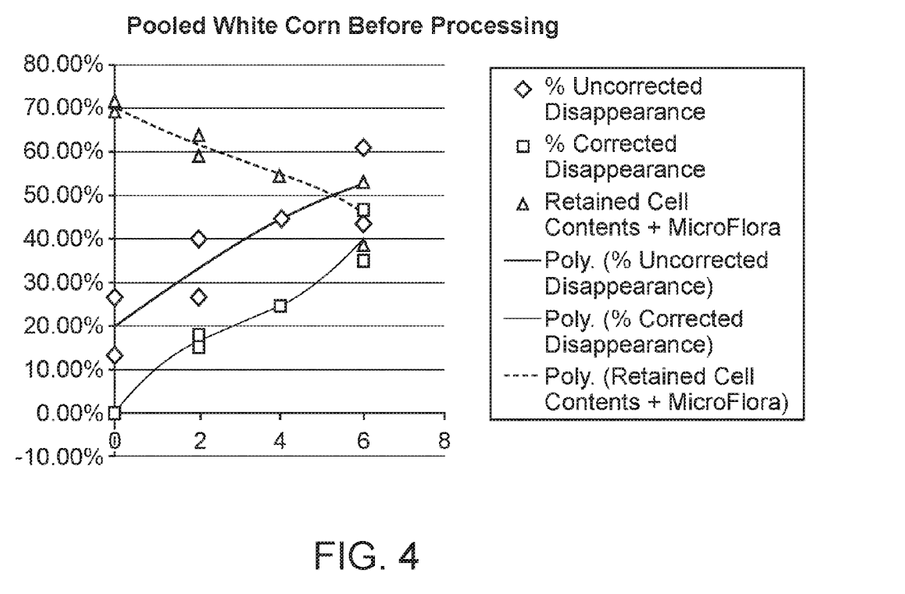
FIG. 4 depicts similar measurements, but for pooled white corn before processing.
Figure 5:
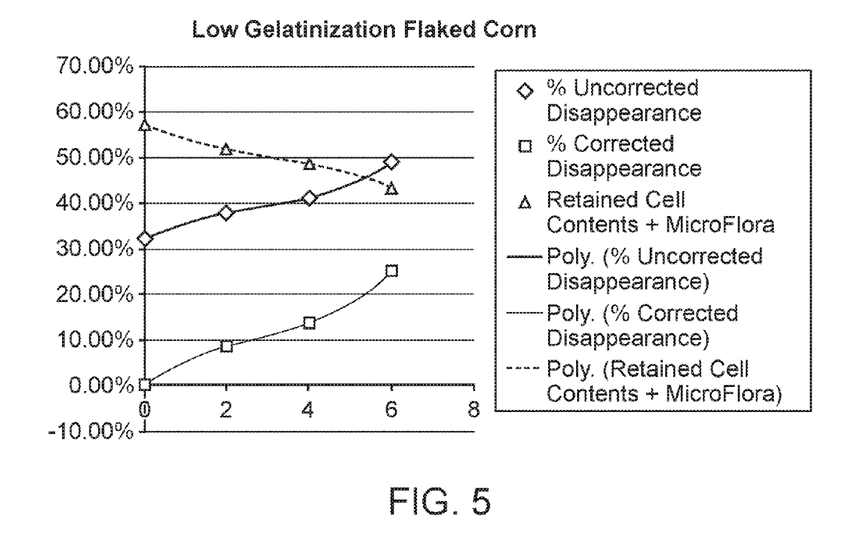
FIG. 5 depicts similar measurements, but for low gelatinization flaked corn.
Figure 6:
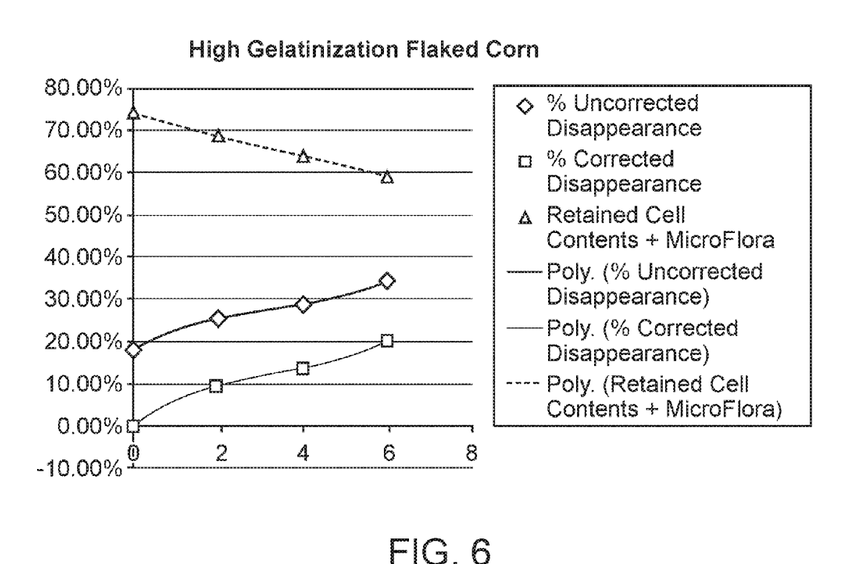
FIG. 6 depicts similar measurements, but for high gelatinization flaked corn.
Figure 7:
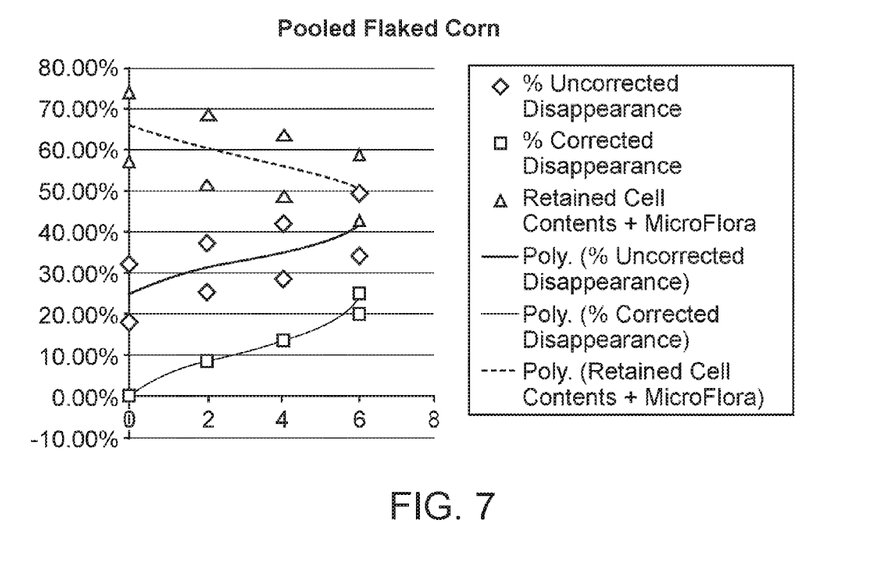
FIG. 7 depicts similar measurements, but for pooled flaked corn.
Figure 8:
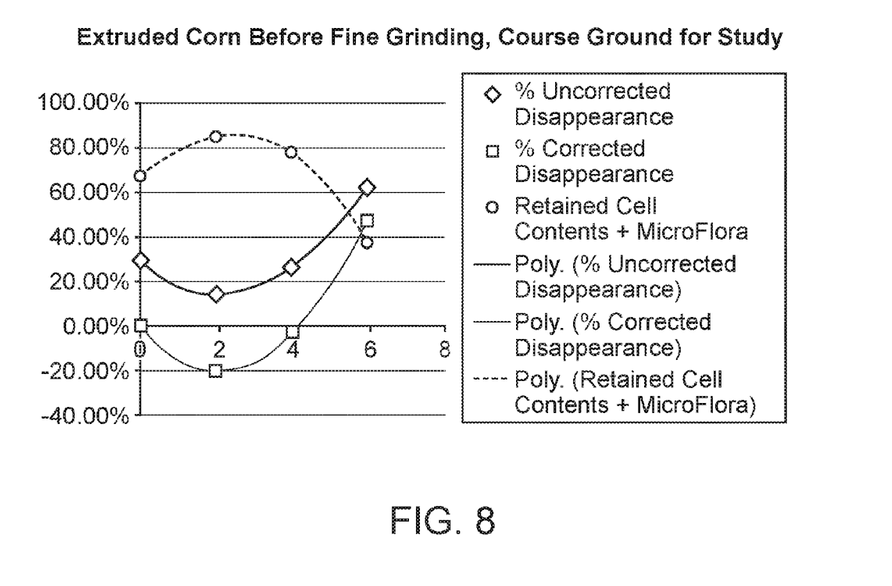
FIG. 8 depicts similar measurements, but for extruded corn, before fine grinding, course ground for study.
Figure 9:
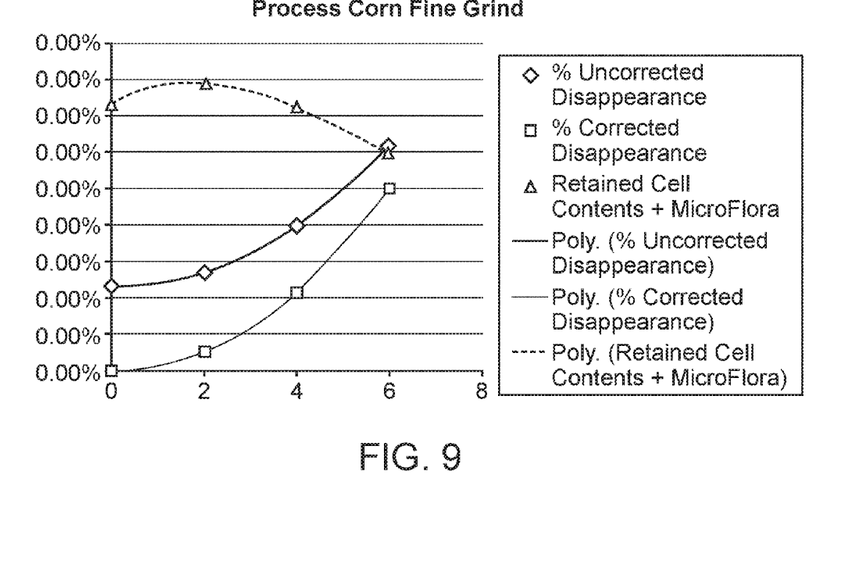
FIG. 9 depicts similar measurements, but for processed corn fine grind.
Figure 10:
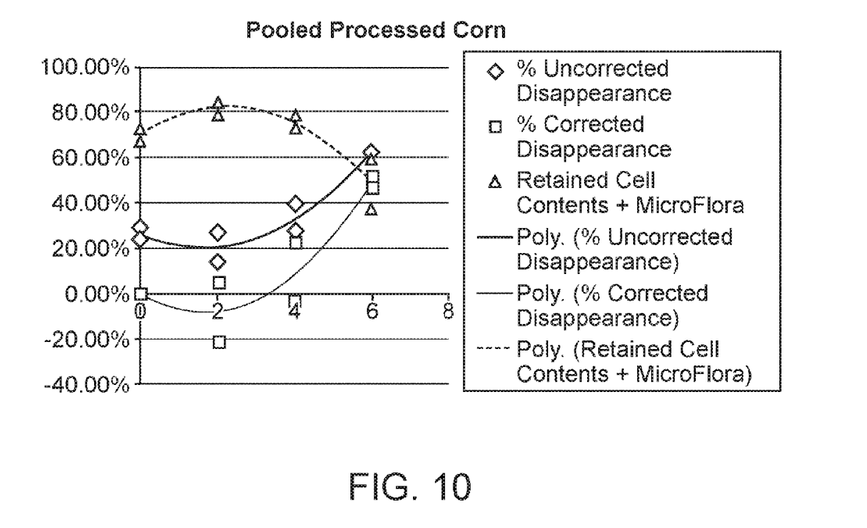
FIG. 10 depicts similar measurements, but for pooled processed corn.
Figure 11:
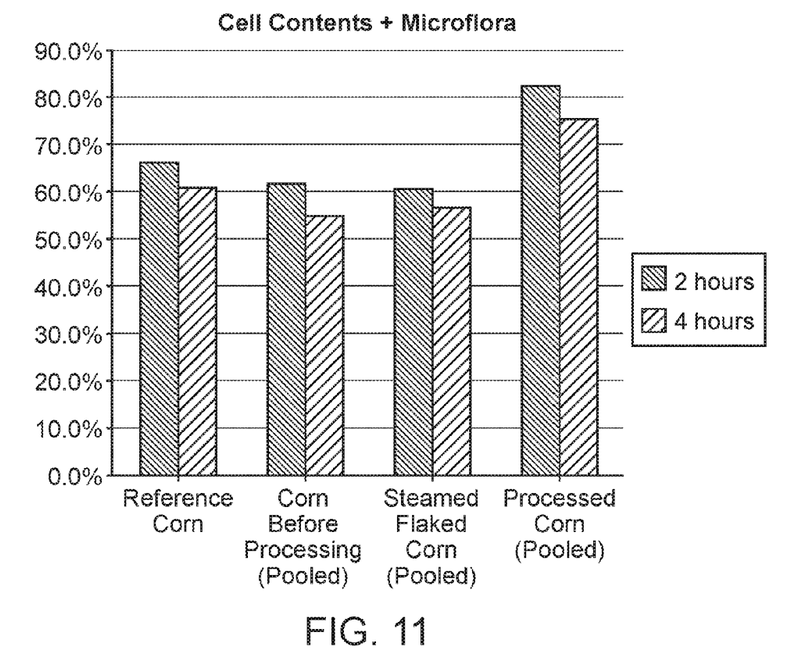
FIG. 11 depicts cell counts and microflora at 2 and 4 hours for variously processed corn.
Figure 12:
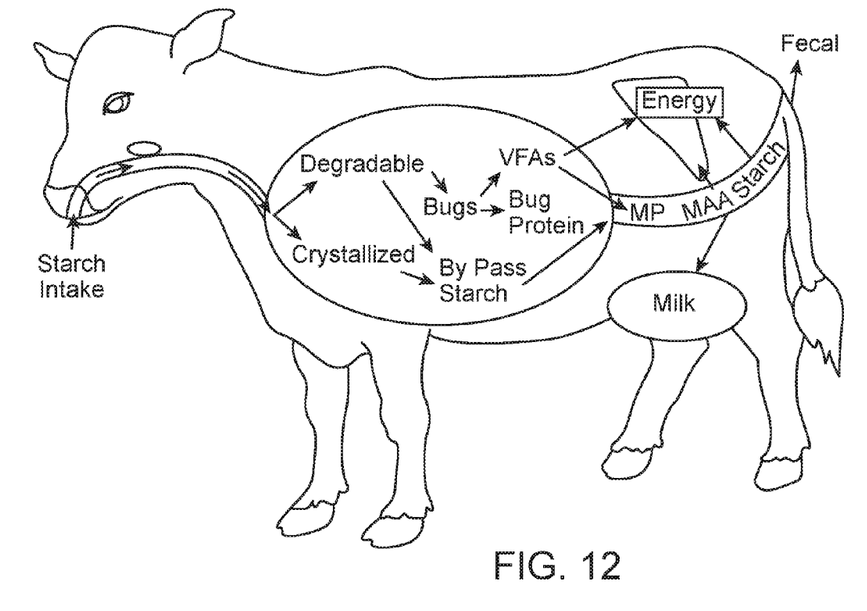
FIG. 12 illustrates a digestive tract of a ruminant depicted as a dairy cow.

As depicted in FIG. 12, in the world of digestion, the ruminant animal is one of the most diverse mammals in the world. Whereas, most mammals contain one stomach, the ruminant has four stomachs and a small intestine with a vast array of organisms with one of the most robust microbiological ecologies on the planet. In these four stomachs, it has been hypothesized that as many as 150,000 organisms reside and are prepared to digest nutritional substrates in vast quantities. The rumen ecology allows them to metamorphose bacteria that distinctly digest the substrate presentation.

Ruminants primarily digest carbon sources in the form of proteins, carbohydrates, fats, sugars and fiber. Ruminants are also unique in that the rumen ecology can ebb and flow regarding digestion and substrates and the ecology based on the substrate presentation. For example, a high corn diet will have a different ratio of bacteria, fungi, volatile fatty acids and protozoa than a high fiber diet.

Operating pH for the ruminant can range from 5.5-6.0, and up to 8.0 with the former representing a high starch/sugar diet and the latter being more fiber forage based. The rumen breaks these carbohydrates and sugars down into volatile fatty acids (VFA) in the form of acetic, lactic, propionic and butyric acid. Once they are broken down they are absorbed through the rumen wall and into the bloodstream.

Long chain fats are biohydrogenated in the rumen and absorbed in the small intestine. Crude protein substrates are hydrolyzed to peptides (chains of amino acids) and deaminated to ammonia. In a dairy animal, we find that most substrates that contribute to milk production are digested in the rumen and not post-ruminal. In a beef animal, primary concern is with digestion across the digestive tract. Post ruminal VFA's contribute less than 5% of the production a dairy animal.

Further complicating digestion by the dairy animal are the bacteria, fungi and protozoa of the rumen that contribute up to 60% of the rumen mass. Most literature and models address the production of bacteria and fungi which have a specific passage rate and a lower level of amino acid contribution. Protozoa have a 6% per hour rumen over rate and contribute up to two times higher levels of essential amino acids such as lysine and Methionine.

In contrast, most monogastric animals (i.e. pigs and chickens) have a pH site digestion in the 2-4 pH range. This allows monogastrics much greater flexibility with regard to substrate digestion starch hardness and biological efficiencies for me production. To confound the digestion efficiency in dairy, the current practices to increase corn production have increased the characteristics of corn which are detrimental to the efficiencies of lactating dairy cattle. These complexities of prolamins, particularly zein in corn can reduce the efficiency of corn up to 60-80% in the rumen and therefore reduce milk production significantly.

DESCRIPTION

In at least one embodiment, a method for processing prolamin-containing feed source into a gelatinous feedstuff is disclosed. The feedstuff is fed to ruminant animals for the purpose of potentiating either milk production or conception, or both. In at least one example, the feed source is corn and the ruminant animal is a bovine, and more specifically, a cow. In one particular example, the animal is a milking cow and pH of its relevant digestive environment is in the range of 5.5 to 8.0. The method includes processing, by extrusion, a prolamin-containing feed source comprising (including, but not limited to) a starch-protein matrix within which the included protein is composed of three percent or greater prolamin. This processing produces a hydrophilic gelatinous feedstuff that has starch and protein content. The hydrophilic gelatinous feedstuff is fed to a ruminant animal. A rumen-retained portion of the fed feedstuff is retained within the rumen of the animal for at least a twenty-four hour period, and during the first twenty-four hours of that period, at least seventy-five percent and up to 99% of the starch content of the rumen-retained portion of the fed feedstuff is digested. The period of retention may be shorter in the instance of fast-transit, high-digestibility starch matrices.

In the present disclosure, the terminology "gelatinous" is defined as non-vitreousness or lowered-vitreousness which indicates an enhanced porosity that enables the rumen fluid bacteria, protozoa and fungi to have complete access to degrade the feedstuff. At least in part, vitreous properties in this disclosure are defined as 2,000 centipoise or less.

In the present disclosure, the terminology "extrusion" defines a process that includes the application of pressure, thermal, mechanical and/or chemical shear (PTMCS) or combination thereof to the feed source to disrupt the prolamin/protein bonds.

Prolamins are a group of plant storage proteins having a high proline content and are found in the seeds of certain cereal grains including wheat (gliadin), barley (hordein), rye (secalin), corn (zein), sorghum (kafirin) and as a minor protein, as avenin in oats. They are characterized by a high glutamine and proline content and are generally soluble only in strong alcohol solutions.

In at least one embodiment, the digested percentage of the starch content of the rumen-retained portion of the fed feedstuff during the first twenty-four hours of the at least twenty-four hour period is at least eighty percent.

In another embodiment, the digested percentage of the starch content of the rumen-retained portion of the fed feedstuff during the first twenty-four hours of the at least twenty-four hour period is at least eighty-five percent.

In another embodiment, the digested percentage of the starch content of the rumen-retained portion of the fed feedstuff during the first twenty-four hours of the at least twenty-four hour period is at least ninety percent.

In another embodiment, the digested percentage of the starch content of the rumen-retained portion of the fed feedstuff during the first twenty-four hours of the at least twenty-four hour period is at least ninety-four percent.

In another embodiment, the digested percentage of the starch content of the rumen-retained portion of the fed feedstuff during the first twenty-four hours of the at least twenty-four hour period is at least ninety-five percent.

In another embodiment, the digested percentage of the starch content of the rumen-retained portion of the fed feedstuff during the first twenty-four hours of the at least twenty-four hour period is at least ninety-eight percent.

In another embodiment, the digested percentage of the starch content of the rumen-retained portion of the fed feedstuff during the first twenty-four hours of the at least twenty-four hour period is at least ninety-eight and six-tenths percent.

In another embodiment, the digested percentage of the starch content of the rumen-retained portion of the fed feedstuff during the first two hours of the at least twenty-four hour period is at least thirty percent.

In another embodiment, the digested percentage of the starch content of the rumen-retained portion of the fed feedstuff during the first two hours of the at least twenty-four hour period is at least thirty-seven percent.

In another embodiment, the digested percentage of the starch content of the rumen-retained portion of the fed feedstuff during the first two hours of the at least twenty-four hour period is at least thirty-seven and three-tenths percent.

In another embodiment, the digested percentage of the starch content of the rumen-retained portion of the fed feedstuff during the first two hours of the at least twenty-four hour period is at least forty percent.

In another embodiment, the digested percentage of the starch content of the rumen-retained portion of the fed feedstuff during the first two hours of the at least twenty-four hour period is at least forty and six-tenths percent.

In another embodiment, the digested percentage of the starch content of the rumen-retained portion of the fed feedstuff during the first six hours of the at least twenty-four hour period is at least seventy percent.

In another embodiment, the digested percentage of the starch content of the rumen-retained portion of the fed feedstuff during the first six hours of the at least twenty-four hour period is at least seventy-eight and three-tenths percent.

In another embodiment, the digested percentage of the starch content of the rumen-retained portion of the fed feedstuff during the first seven hours of the at least twenty-four hour period is at least eighty percent.

In another embodiment, the digested percentage of the starch content of the rumen-retained portion of the fed feedstuff during the first seven hours of the at least twenty-four hour period is at least ninety-one and four-tenths percent.

In another embodiment, the digested percentage of the starch content of the rumen-retained portion of the fed feedstuff during the first twelve hours of the at least twenty-four hour period is at least seventy-five percent.

In another embodiment, the digested percentage of the starch content of the rumen-retained portion of the fed feedstuff during the first twelve hours of the at least twenty-four hour period is at least eighty-five and two-tenths percent.

In another embodiment, the extrusion process ruptures the prolamin bonds thereby rendering at least ninety-eight percent of the starch content of the hydrophilic resulting gelatinous feedstuff digestible in the rumen of ruminant animals, which is also referred to as Rumen Available Starch (RAS) which is a one hundred percent rumen digestible, site specific form of starch.

In another embodiment, a viscosity of the hydrophilic resulting gelatinous feedstuff is less than 2000 Centipoise. In another aspect, the hydrophilic resulting gelatinous feedstuff can be characterized as possessing less than 50% of the viscosity value of the corresponding non-treated substrate.

In another embodiment, conception rates are increased in a ruminant animal fed the hydrophilic gelatinous feedstuff during periods of potential heat stress when ambient temperatures daily exceed ninety degrees Fahrenheit.

In another embodiment, the likelihood of conception of a ruminant animal fed the hydrophilic gelatinous feedstuff is at least doubled during periods of heat stress when ambient temperatures daily exceed one-hundred degrees Fahrenheit.

In another aspect, the presently disclosed processing of the feed source increases the uptake of starch by Entodinia protozoa, propagation of the latter, and which increases the output to the small intestine of high quality essential amino acids to the small intestine (i.e. lysine, methionine, cysteine).

A production method and resulting feedstuff composition for ruminant animals is disclosed and includes: the manufacture of feed from grains containing prolamine; the manufacture of feed with a defined characteristic from high prolamine grains; a method for rupturing the starch prolamine matrix for a feedstuff; and a method of preparing a feed to improve the performance and/or feed utilization by microorganisms and/or animals.

Animal feeding operations house groups of animals that are fed together with the goal of maximizing their growth, while minimizing their food intake. Typically, the feed is generally composed of starch and protein containing substances. In many cases, corn, processed corn or by-products of corn processes and fermentations of corn are fed to animals. Similarly, the original starch/protein source can be sorghum or another type of grain. Corn is typically favored for its relatively high nutrient and starch composition, as well as low cost.

The availability of the starch, protein and other nutrients from the grains can be improved by increasing the surface area of the feedstuff by grinding, milling and flaking the original material. The overall digestibility of corn in particular can also be improved by applying heat and/or heat under pressure. Still further, digestability of corn can also be improved by hydrating it.

Lactating dairy cows have four stomachs for digestion of feedstuffs, however, the rumen is the most important for milk production as it is the area where most components (i.e. starch, protein and fiber) are broken down for milk production. It has been concluded through research that 80-95% of the starch broken down in the rumen contributes to Volatile Fatty Acid (VFA) production, and which is further broken down into milk production. Further, properly processed starch that is available in the rumen can also contribute to the production of microbial protein that is the primary source of protein produced by the cow for milk synthesis.

Most conventional starch sources fed to dairy cattle are moderately processed through steam heating and flaking and produce products in which only one-third of the starch is degraded in the rumen. Further, in the last 30 years of corn breeding, the characteristics of corn have been selected to produce grain that is: harder, higher in zein proteins (a protein matrixed with starch that reduces digestibility to dairy cattle), higher in test weights, faster to dry, has fewer fines, is more hydrophobic instead of hydrophilic, and is higher yielding. Each of these characteristics are detrimental to the digestion of starch in the rumen which breaks the starch down at a pH of 6.0-7.5, as opposed to a monogastric (i.e. chicken, pig, layer, turkey) that can digest these new corn varieties because the pH in their digestive tracts can be as low as 2-3. Further, the digestion sites in the monogastric, as well as a production beef cow is across the total digestive tract and does not necessarily have to be site specific in the breakdown of starch and protein to optimize the animals' production.

In ruminants, the most efficient manner to produce milk with the currently available substrates is to make the starch fraction more available in the rumen in a form that is vitreous enough to adhere to the particles in the rumen and can completely degrade before leaving the rumen. This yields the most efficient use of starch sources and increases the production of protein in the rumen, thereby sparing the waste of starch sources and increasing the endogenous production of protein to the dairy animal. This will increase milk production with the least amount of nutrients and reduce the excretion of excess nitrogen and the global footprint of dairy cows worldwide.

The present description discloses, among other things, such as a manufacturing process for, and the resulting feedstuff therefrom that provides a highly digestible starch source by changing the properties of the zein/starch matrix to be hydrophilic from hydrophobic. Minimally, this is accomplished by processing a ground starch source (ground corn, sorghum, wheat, rye or other grain, for example) in a pressure vessel at between 7-40 psi and a temperature of 200-325 degrees Fahrenheit for a time period of one-half to five minutes in dependence upon the starch/zein matrix of the starch source. Further processing includes extrusion in which mechanical pressure and shear is applied until the matrix has been gelatinized to between approximately 70-100 percent. The resulting product has vitreous properties that enhance the digestion of the original starch source by the fed animal.

As an example, an end product is created that has vitreous properties that enhance the absorption of rumen fluid and bacteria which enhance the breakdown of starch within the rumen. The breakdown of this starch is found to be an inverted parabola digestion curve as opposed to a curvilinear digestion curve which means that the degradation rate initially drops versus conventional starch, and then degrades rapidly because of vitreous and hydrophilic properties enhanced by the production properties. These digestion curves and relationships are found in the accompanying FIGS. 1-10 which show graphical figures that compare the digestion curves of conventional starch sources of ground corn and flaked corn.

Further modeling through the Cornell Nutrition Carbohydrate Protein System (CNCPS) has shown the process to increase degradation curves two to three times over conventional starch sources, and enhance the ability to contribute to protein synthesis thereby reducing the need for exogenous protein sources by 15-35% which also reduces nitrogen excretion by dairy cows.

Consistency in animal feed products, particularly for ruminant animals, and especially for beef cattle and dairy cows is highly desired and the resulting product of the process described above preferably has the following characteristics: consistent starch/protein/nutrient composition even with varied starting levels of prolamine and starch content; over 50% is digested within eight hours in the gastrointestinal tract; and stable chemical composition that resists degrading under storage conditions.

In ruminant animals, starch is variably processed: some is degraded in the rumen and grows bugs (bacteria); some makes VFA and microbial protein; some escapes the rumen before it can be degraded; some is utilized as an energy source; some goes to the large intestine before it can be absorbed; some grows bugs and provides VFA, but no protein to the cow; and some is indigestible by the animal and ends up in the manure.

The endosperm of corn is a starch protein matrix that comprises four types of protein: albumins, globulins, glutelins, and prolamines. Prolamines in corn are referred to as zein and make-up approximately 50-60% of the protein in corn. The amino-acid in prolamines makes the corn hydrophobic and therefore not Soluble in water or rumen fluid. As such, prolamines have industrial applicability in such things as edible, biodegradable plastic.

Additional prolamine characteristics include that it forms on the starch granule surface; its proteins can cross-link; it encapsulates starch into a matrix; it advances with maturity like NDF in forages; and, it can have genetic differences in corn. Relatedly, floury/opaque corns are missing the Y-zein gene and are low in prolamines. Flint corns are very high in prolamines. Common corn hybrids are moderately-high in prolamines. For comparison, barley (hordein) and oats (avenin) are low in prolamines, wheat (gliadin) and rye (secalin) are med-low in prolamines, corn (zein) is high and sorghum (kafirin) is very hight in prolamines.

Extruding corn is superior to rolling and flaking corn which does not physically change the starch/prolamine content of the corn. Further, as flakes of corn sit in inventory, the starch retrogrades in that it becomes more crystalline, which is indigestible and must be used within 2-3 days of production.

Extrusion as a processing method for corn is superior because it increases consistency. Extrusion also physically/chemically disrupts the starch/prolamine relationship and it does not retrograde. Extrusion increases shelf life, post processing, which increases the possibility that corn can be extruded at a central location and then shipped out. That is to say, extruded corn is "shelf stable".

TABLE 1

| Corn Composition | |
|---|---|
| Dry Matter | 89 |
| Crude Protein | 9.1 |
| NDF | 9.9 |
| Lignin | 1.2 |
| Sugar | 2.5 |
| Starch | 70 |
| Total digestible nutrients | 88 |

Some of the benefits and characteristics of corn extruded according to this disclosure, and its utilization as a feed for ruminants, include: (1) decreased DMI (Dry Matter Intake); (2) increased milk yield; (3) changes in hepatic oxidation; (4) decreases heat stress; (5) decreases passage rate of starch; (6) increases microbial utilization of starch; (7) increases microbial protein production in the rumen; (8) increases microbial protein production in the intestine; (9) alters starch digestion curves; (10) increases the utilization of zein; (11) increases utilization of prolamine; (12) fosters site-specific (rumen/intestine/hindgut) digestion of the processed feed; (13) fosters digestion of the feed in the rumen by microorganisms; (14) increases surface area of the processed feed; (15) chemically modifies starch and protein composition; (16) decreases intestinal digestion of starch; (17) alters VFA profiles in the rumen; and (18) increases VFA production in the rumen and decreases VFA production in the hindgut.

A production method and resulting feedstuff composition for ruminant animals is disclosed in and includes: the manufacture of feed from grains containing prolamine; the manufacture of feed with a defined characteristic from high prolamine grains; a method for rupturing the starch prolamine matrix for a feedstuff; and a method of preparing a feed to improve the performance and/or feed utilization by microorganisms and/or animals.

What is claimed is:

1. A method of producing and feeding a feedstuff to a dairy cow and thereby potentiating milk production, the method comprising:
   heat-treating corn having a vitreousness of at least 66% for a period of at least 1200 seconds, the last 200 seconds of which is maintained above 90 degrees Celsius, thereafter extruding the corn and applying sufficient shear pressure to disrupt the prolamin/protein bonds and thereby obtaining an extruded hydrophilic, low-vitreous, gelatinous feedstuff comprising a starch and protein matrix composed of at least three percent prolamin; and
   feeding the feedstuff to a restrained dairy cow and thereby causing a portion of the feedstuff to be rumen-retained within the rumen of the animal for at least a twenty-four hour period such that during the first twenty-four hours of that period, at least seventy-five percent of the starch content of the rumen-retained portion of the fed feedstuff is digested.

2. The method as recited in claim 1, wherein the digested percentage of the starch content of the rumen-retained portion of the fed feedstuff during the first twenty-four hours is at least eighty percent.

3. The method as recited in claim 1, wherein the digested percentage of the starch content of the rumen-retained portion of the fed feedstuff during the first twenty-four hours is at least eighty-five percent.

4. The method as recited in claim 1, wherein at least thirty percent of the starch content digested in the first twenty-four hour period is digested during the first two hours of the first twenty-four hour period.

5. The method as recited in claim 1, wherein at least thirty five percent of the starch content digested in the first twenty-four hour period is digested during the first two hours of the first twenty-four hour period.

6. The method as recited in claim 1, wherein at least thirty-seven and three-tenths percent of the starch content digested in the first twenty-four hour period is digested during the first two hours of the first twenty-four hour period.

7. The method as recited in claim 1, wherein at least forty percent of the starch content digested in the first twenty-four hour period is digested during the first two hours of the first twenty-four hour period.

8. The method as recited in claim 1, wherein at least forty and six-tenths percent of the starch content digested in the first twenty-four hour period is digested during the first two hours of the first twenty-four hour period.

9. The method as recited in claim 1, wherein at least seventy percent of the starch content digested in the first twenty-four hour period is digested during the first six hours of the first twenty-four hour period.

10. The method as recited in claim 1, wherein at least seventy-eight and three-tenths percent of the starch content digested in the first twenty-four hour period is digested during the first six hours of the first twenty-four hour period.

11. The method as recited in claim 1, wherein at least eighty percent of the starch content digested in the first twenty-four hour period is digested during the first seven hours of the first twenty-four hour period.

12. The method as recited in claim 1, wherein at least ninety-one and four-tenths percent of the starch content digested in the first twenty-four hour period is digested during the first seven hours of the first twenty-four hour period.

13. The method as recited in claim 1, wherein at least seventy-five percent of the starch content digested in the first twenty-four hour period is digested during the first twelve hours of the first twenty-four hour period.

14. The method as recited in claim 1, wherein at least eighty-five and two-tenths percent of the starch content digested in the first twenty-four hour period is digested during the first twelve hours of the first twenty-four hour period.

15. The method as recited in claim 1, wherein the extruded hydrophilic, low-vitreous, gelatinous feedstuff comprises a sufficient proportion of ruptured prolamin bonds whereby at least ninety-eight percent of the starch content of the feedstuff is rendered digestible in the rumen of ruminant animals.

16. The method as recited in claim 1, wherein a viscosity of the hydrophilic, low-vitreous gelatinous feedstuff is less than 2000 Centipoise.

17. The method as recited in claim 1, further comprising increasing conception rates in a ruminant animal fed the hydrophilic low-vitreous, gelatinous feedstuff during periods of potential heat stress when ambient temperatures daily exceed ninety degrees Fahrenheit.

18. The method as recited in claim 1, further comprising at least doubling the likelihood of conception of a ruminant animal fed the hydrophilic low-vitreous, gelatinous feedstuff during periods of heat stress when ambient temperatures daily exceed one-hundred degrees Fahrenheit.

19. The method as recited in claim 1, further causing an increase in the uptake of starch granules in *Entodinia* sp. rumen protozoa whereby higher propagation rates, lysis and delivery to the animal's small intestine of high quality essential amino acids is affected.

20. A method of feeding an extruded feedstuff to a ruminant animal and thereby potentiating at least one of milk production and conception, the method comprising:
obtaining an extruded, heat-treated corn having a vitreousness of at least 66% that has been heat-treated for a period of at least 1200 seconds, the last 200 seconds of which is maintained above 90 degrees Celsius and after which sufficient shear pressure has been applied by extrusion to disrupt the prolamin/protein bonds thereby producing an extruded hydrophilic, low-vitreous, gelatinous feedstuff comprising a starch and protein matrix composed of at least three percent prolamin; and
feeding the feedstuff to a ruminant animal and thereby causing a portion of the feedstuff to be rumen-retained within the rumen of the animal for at least a twenty-four hour period such that during the first twenty-four hours of that period, at least seventy-five percent of the starch content of the rumen-retained portion of the fed feedstuff is digested.

21. A method of feeding an extruded feedstuff to a ruminant animal, the method comprising:
feeding to a ruminant animal an extruded, hydrophilic, low-vitreous, gelatinous heat-treated feedstuff comprising corn having a vitreousness of at least 66% that has been heat-treated for a period of at least 1200 seconds, the last 200 seconds of which is maintained above 90 degrees Celsius and after which sufficient shear pressure has been applied by extrusion to disrupt the prolamin/protein bonds whereby the extruded, hydrophilic, low-vitreous, gelatinous heat-treated feedstuff comprises a starch and protein matrix composed of at least three percent prolamin and has a viscosity value less than 2000 Centipoise, and thereby causing a portion of the feedstuff to be rumen-retained within the rumen of the animal for at least a twenty-four hour period such that during the first twenty-four hours of that period, at least seventy-five percent of the starch content of the rumen-retained portion of the fed feedstuff is digested.

22. A method of producing a feedstuff for feeding to a dairy cow and thereby potentiating milk production, the method comprising:
heat-treating corn for a period of at least 1200 seconds, of which 200 seconds is maintained above 90 degrees Celsius, thereafter extruding the corn and applying sufficient shear pressure to disrupt the prolamin/protein bonds and thereby obtaining an extruded hydrophilic, low-vitreous, gelatinous feedstuff comprising a starch and protein matrix composed of at least three percent prolamin; and whereby the feedstuff, when fed to a dairy cow results in a portion of the feedstuff being rumen-retained within the rumen of the animal for at least a twenty-four hour period such that during the first twenty-four hours of that period, at least seventy-five percent of the starch content of the rumen-retained portion of the fed feedstuff is digested.

23. The method of claim 22, further comprising the corn having a vitreousness of at least 66% prior to being heat-treated.

24. The method as recited in claim 22, wherein a viscosity value of the extruded hydrophilic, low-vitreous gelatinous feedstuff is less than 2000 Centipoise.

25. The method as recited in claim 22, wherein a viscosity value of the extruded hydrophilic, low-vitreous gelatinous feedstuff is less than 50% of the viscosity value of the heat-treated corn before extrusion.

26. The method of claim 22, further comprising feeding the extruded hydrophilic, low-vitreous, gelatinous feedstuff to a ruminant animal.

27. The method of claim 26, further comprising causing a portion of the feedstuff to be rumen-retained within the rumen of the animal for at least a twenty-four hour period such that during the first twenty-four hours of that period, at least seventy-five percent of the starch content of the rumen-retained portion of the fed feedstuff is digested.

28. The method of claim 26, further comprising causing an increase in the uptake of starch granules in *Entodinia* sp. rumen protozoa whereby higher propagation rates, lysis and delivery to the animal's small intestine of high quality essential amino acids is affected.

29. The method of claim 26, further comprising causing at least a doubling of the likelihood of conception of a ruminant animal fed the feedstuff during periods of heat stress when ambient temperatures exceed one-hundred degrees Fahrenheit.

30. A method of producing a feedstuff for feeding to a dairy cow and thereby potentiating milk production, the method comprising:
a multi-stage process comprising a first stage in which a feed corn for dairy cattle is heat-treated for a first period of time, of which at least 200 seconds is maintained above 90 degrees Celsius, and thereafter extruding the corn in a second stage by applying sufficient shear pressure to disrupt the prolamin/protein bonds and thereby producing an extruded hydrophilic, low-vitreous, gelatinous feedstuff comprising a starch and protein matrix composed of at least three percent prolamin.

31. The method as recited in claim 30, wherein a viscosity value of the extruded hydrophilic, low-vitreous gelatinous feedstuff is less than 2000 Centipoise.

32. The method as recited in claim 30, wherein a viscosity value of the extruded hydrophilic, low-vitreous gelatinous feedstuff is less than 50% of the viscosity value of the heat-treated corn before extrusion.

33. The method of claim 30, wherein, when the feedstuff is fed to a dairy cow, a portion of the feedstuff is rumen-retained within the rumen of the animal for at least a twenty-four hour period such that during the first twenty-four hours of that period, at least seventy-five percent of the starch content of the rumen-retained portion of the fed feedstuff is digested.

34. The method of claim 30, wherein, in the first stage of the multi-stage process, the corn is heat-treated for a period of at least 1200 seconds.

35. The method of claim 34, wherein the at least 200 second period during which the heat treatment is maintained above 90 degrees Celsius is the last 200 seconds of the at least 1200 second long first stage of heat treatment.

36. The method of claim 30, further comprising the corn having a vitreousness of at least 66% prior to being heat-treated.

* * * * *